(12) United States Patent
Berens et al.

(10) Patent No.: US 8,796,481 B2
(45) Date of Patent: Aug. 5, 2014

(54) CRYSTALLINE SOLVATE AND NON-SOLVATED FORMS OF 6,6'-[[3,3',5,5'-TETRAKIS(1,1-DIMETHYLETHYL)-[1,1'BIPHENYL]-2,2'-DIYL]BIS(OXY)]BIS-DIBENZO [D,F] [1,3,2]-DIOXAPHOSPHEPINE

(71) Applicant: BASF SE, Ludwigshafen (DE)

(72) Inventors: Ulrich Berens, Binzen (DE); Holger Ganz, Ludwigshafen (DE); Tiziana Chiodo, Mannheim (DE)

(73) Assignee: BASF SE (DE)

( * ) Notice: Subject to any disclaimer, the term of this patent is extended or adjusted under 35 U.S.C. 154(b) by 0 days.

(21) Appl. No.: 13/728,350

(22) Filed: Dec. 27, 2012

(65) Prior Publication Data

US 2013/0184478 A1 Jul. 18, 2013

Related U.S. Application Data

(60) Provisional application No. 61/581,657, filed on Dec. 30, 2011.

(51) Int. Cl.
*C07F 15/00* (2006.01)
*C07F 9/02* (2006.01)

(52) U.S. Cl.
USPC .............................................. 556/13; 558/78

(58) Field of Classification Search
USPC ............................................ 556/13; 558/78
See application file for complete search history.

(56) References Cited

U.S. PATENT DOCUMENTS

| 4,668,651 A | 5/1987 | Billig et al. |
|---|---|---|
| 4,748,261 A | 5/1988 | Billig et al. |
| 4,769,498 A | 9/1988 | Billig et al. |
| 4,885,401 A | 12/1989 | Billig et al. |
| 5,235,113 A | 8/1993 | Sato et al. |
| 5,312,996 A | 5/1994 | Packett |
| 5,391,801 A | 2/1995 | Sato et al. |
| 5,663,403 A | 9/1997 | Sato et al. |
| 5,688,986 A | 11/1997 | Tam et al. |
| 5,728,861 A | 3/1998 | Sato et al. |
| 6,172,267 B1 | 1/2001 | Urata et al. |
| 7,351,339 B2 | 4/2008 | Maase et al. |
| 2003/0100787 A1 | 5/2003 | Akbarali et al. |
| 2007/0112219 A1 | 5/2007 | Ortmann et al. |
| 2008/0083606 A1 | 4/2008 | Volland et al. |

FOREIGN PATENT DOCUMENTS

| CN | 101684130 A | 3/2010 |
|---|---|---|
| CN | 102432638 A | 5/2012 |
| DE | 10360771 A1 | 7/2005 |
| EP | 0214622 A2 | 3/1987 |
| EP | 0285136 A2 | 10/1988 |
| EP | 0577042 A1 | 1/1994 |
| EP | 0730574 A1 | 9/1996 |
| JP | 09077713 | 3/1997 |
| WO | WO-03062171 A2 | 7/2003 |
| WO | WO-03062251 A1 | 7/2003 |
| WO | WO-2010042313 A1 | 4/2010 |
| WO | WO-2013/066712 | 3/2013 |

OTHER PUBLICATIONS van Rooy et al., Organometallics, vol. 15, No. 2, pp. 835-847 (1996).*
Van Rooy, Annemiek, et al., "Bulky Diphosphite-Modified Rhodium Catalysts: Hydroformylation and Characterization", Organometallics, vol. 15, (1996), pp. 835-847.
International Search Report and Written Opinion from corresponding PCT/EP2012/077021 dated Feb. 25, 2013.

* cited by examiner

*Primary Examiner* — Porfirio Nazario Gonzalez
(74) *Attorney, Agent, or Firm* — Drinker Biddle & Reath LLP (57) ABSTRACT

The present invention relates to a crystalline non-solvated form of 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepine (compound I) and toluene-solvates and acetone-solvates thereof.

28 Claims, 6 Drawing Sheets

Figure 1
(toluene-monosolvate)

Figure 2
(toluene-monosolvate)

Figure 3
(non-solvate)

Figure 4
(acetone-solvate "A")

CRYSTALLINE SOLVATE AND NON-SOLVATED FORMS OF 6,6'-[[3,3',5,5'-TETRAKIS(1,1-DIMETHYLETHYL)-[1,1'BIPHENYL]-2,2'-DIYL]BIS(OXY)]BIS-DIBENZO [D,F] [1,3,2]-DIOXAPHOSPHEPINE

CROSS-REFERENCE TO RELATED APPLICATIONS

This application claims benefit (under 35 USC 119(e)) of U.S. Provisional Application 61/581,657, filed Dec. 30, 2011, which is incorporated by reference.

FIELD OF THE INVENTION 6,6'-[[3,3',5,5'-Tetrakis(1,1-dimethylethyl)-[1,1'-biphenyl]-2,2'-diyl]bis(oxy)]bis-dibenzo[d,f][1,3,2]-dioxaphosphepine (in the following also denoted as "compound I") is used as ligand of homogeneous catalysts, in particular in rhodium catalysts for the hydroformylation of olefins. The chemical structure of compound I is shown by the following formula:

The present invention relates to novel crystalline forms of 6,6'-[[3,3',5,5'-tetrakis(1,1-dimethylethyl)-[1,1'-biphenyl]-2,2'-diyl]bis(oxy)]bis-dibenzo[d,f][1,3,2]-dioxa-phosphepine, methods for their production and their use.

For the application properties of substances that are used on the industrial scale, the possible existence of crystalline modifications (also known as crystalline forms) or of solvates of the substance in question, the knowledge of the specific properties of such modifications and solvates and of methods for their preparation is in many cases of decisive importance. A substance can exist in different crystalline modifications but also in amorphous form. These cases are referred to as polymorphism. A polymorph is a solid, crystalline phase of the compound, which is characterized by a defined, uniform, packing and arrangement of the molecules in the solid substance. Different modifications of one and the same substance display different properties, for example differences in the following properties: crystal shape and size, density, solubility, filterability, dissolution rate, stability to phase conversion into another modification, stability during milling, suspension stability, optical and mechanical properties, vapor pressure, hygroscopicity, melting point, stability to decomposition, or color.

Organic bisphosphite compounds of the type of compound I, their preparation and use as ligand in the homogeneous catalysis are described e.g. in EP 0 214 622 A2, U.S. Pat. Nos. 4,668,651, 4,748,261, 4,769,498, 4,885,401, 5,235,113, 5,391,801, 5,663,403, 5,728,861, 6,172,267, DE 103 60 771 A1, WO 2003/062171 and WO 2003/062251.

WO 2010/042313 describes a step-wise process for the preparation of a bisphosphite. In step (a) a phosphoromonochloridite is prepared by reacting $PCl_3$ with an aromatic diol in a slurry under reaction conditions and in the presence of a second aromatic diol to produce a mixture comprising the phosphoromonochloridite, the second aromatic diol, and excess $PCl_3$. The slurry comprises less than 5 mole percent of a nitrogen base, and the organic solvent is selected for its low hydrogen chloride solubility. After removing the excess $PCl_3$, a nitrogen base is added to effect condensation of the phosphoromonochloridite with the second aromatic diol to yield the bisphosphite. A purification by recrystallization is only described in very general terms.

EP 0 285 136 A2 describes a process for separating secondary organophosphites from tertiary organophosphites which comprises (1) treating a composition consisting essentially of tertiary and secondary organophosphites dissolved in an organic solvent, with added water and a base to selectively convert the secondary organophosphite to a salt and (2) separating and recovering the tertiary organophosphite from said salt. In comparative examples 8, 28 and 29, a crude tertiary monophosphite (phosphite B), comprising a mixture of the tertiary and a secondary organophosphate as impurity, is recrystallized from acetonitrile.

US 2003/0100787 describes a process for producing sterically hindered triarylphosphites. The reaction product is precipitated out of iso-propanol. There is no incentive to employ a corresponding process for producing bisphosphite compounds.

CN 101684130A describes a process for preparing organic bisphosphite compounds wherein
a.) the phosphoromonochloridite forming the side wings is dissolved in dichloromethane,
b.) the aromatic diol forming the bridging group is dissolved in triethylamine or triethylamine/dichloromethane,
c.) the solutions are mixed and reacted at −40° C. to 20° C.,
d.) the obtained solution is stirred at 20 to 30° C. for 10 to 20 h, and
e.) deionized water is added to the solution obtained in step d.) to induce a phase separation, wherein the lower organic phase contains the product.
It is further described to recrystallize the obtained bisphosphite from hexane.

U.S. Pat. No. 5,312,996 regards to a hydroformylation process for producing 1,6-hexanedials. In column 18, line 60 fol. the preparation of several ligands, inter alia of compound I (=ligand A) is described, using the reaction of 1,1'-biphenyl-3,3'-di-tert.-butyl-5,5'-di-tert.-butoxy-2,2'-diol with biphenol chloridite as an example. The resulting reaction solution is concentrated to a syrup on a rotary evaporator and acetonitrile was added to precipitate the bisphosphite ligand. The mixture was stirred for 2 h at room temperature, filtered, the solids washed with acetonitrile and dried under vacuum. The described procedure is not suitable for producing a crystalline non-solvated form of compound I. The inventors of the present invent have found that from compound I and acetonitrile at room temperature an acetonitrile-solvate is obtained. Nevertheless, the presence of acetonitrile in the crystal lattice is detrimental to a use as ligands for the homogeneous catalysis as acetonitrile coordinates to the employed transition metals and thus interferes with the catalysis.

A. van Rooy et al. describe in Organometallics 1996, 15(2), 835-847 studies of the hydroformylation and the characterization of bulky diphospite-modified rhodium catalysts. A preparation of compound I (=ligand 9) is described, wherein the product is obtained by precipitation with acetonitrile, recrystallized from toluene/acetonitrile and dried in vacuo. More detailed conditions of the recrystallization are not provided and the product has not been characterized by crystallographic data.

Compounds I prepared according to such known methods show at least one of the following disadvantages: the product is sticky, tends on long term storage to caking or tends to the formation of dust. Such properties have a negative effect on the suitability for the use of those compounds on an industrial scale, e.g. for the manufacture of catalysts.

It has now surprisingly been found that by defined processes a previously unknown crystalline, stable non-solvate modification of 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepine, which does not display the disadvantages of the known solid forms, is obtained in high purity. In addition, four crystalline solvates of 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepine, with comparable advantageous properties were found.

SUMMARY OF THE INVENTION

A first object of the present invention relates to a crystalline non-solvated form and a crystalline toluene-solvate and crystalline acetone-solvates of 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepine.

A further object of the present invention relates to a crystalline toluene-monosolvate of 6,6'-[[3,3',5,5'-tetrakis(1,1-dimethylethyl)-[1,1'-biphenyl]-2,2'-diyl]bis(oxy)]bis-dibenzo [d,f][1,3,2]-dioxaphosphepine, which in an X-ray powder diffractogram at 25° C. with Cu—Kα radiation displays at least 5 of the following reflections, stated as 2θ values: 5.15±0.20°, 7.59±0.20°,8.56±0.20°,8.80±0.20°,8.97±0.20°,9.65±0.20°,10.55±0.20°, 11.47±0.20°,14.76±0.20° and 15.35±0.20.

A further object of the invention relates to a non-solvated crystalline form of 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepine, which in an X-ray powder diffractogram at 25° C. with Cu—Kα radiation displays at least 5 of the following reflections, stated as 2θ values: 5.39±0.20°, 7.04±0.20°, 8.44±0.20°, 8.65±0.20°, 9.08±0.20°, 9.66±0.20°, 10.66±0.20°, 12.60±0.20°, 16.25±0.20° and 17.36±0.20°.

A further object of the invention relates to a crystalline acetone-solvate "A" of 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepine, which in an X-ray powder diffractogram at 25° C. with Cu—Kα radiation displays at least 5 of the following reflections, stated as 2θ values: 6.67±0.20°, 7.11±0.20°, 7.87±0.20°, 8.31±0.20°, 8.96±0.20°, 9.17±0.20°, 10.68±0.20°, 15.78±0.20°, 16.10±0.20° and 18.63±0.20°.

A further object of the invention relates to a crystalline acetone-solvate "b" of 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepine, which in an X-ray powder diffractogram at 25° C. with Cu—Kα radiation displays at least 5 of the following reflections, stated as 2θ values: 8.13±0.2, 8.70±0.2°, 8.95±0.2°, 10.02±0.2°, 10.98±0.2°, 11.71±0.2°, 14.16±0.2°, 15.65±0.2°, 16.98±0.2° and 18.08±0.2°.

A further object of the invention relates to a crystalline acetone-solvate "C" of 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepine, which in an X-ray powder diffractogram at 25° C. with Cu—Kα radiation displays at least 5 of the following reflections, stated as 2θ values: 5.40±0.20°, 6.97±0.20°, 7.64±0.20°, 8.39±0.20°, 9.24±0.20°, 9.44±0.20°, 11.23±0.20°, 13.46±0.20°, 15.32±0.20° and 18.35±0.20°.

Further objects of the invention are processes for the preparation of the crystalline forms of compound I.

A further object of the invention is the use of a crystalline form of compound I, as defined above and in the following, for the production of a transition metal catalyst for hydroformylation, hydrocyanation or hydrogenation.

A further object of the invention is a method for producing a transition metal catalyst, wherein a crystalline form of compound I, as defined above and in the following, is provided and brought into contact with a compound or a complex of a transition metal in an inert solvent.

A further object of the invention is a transition metal catalyst, obtainable by a method wherein a crystalline form of compound I, as defined above and in the following, is provided and brought into contact with a compound or a complex of a transition metal in an inert solvent.

DETAILED DESCRIPTION OF THE INVENTION

The crystalline forms of compound I according to the invention have the following advantages:
low tackiness,
lower tendency to cake,
lower tendency of dust formation,
high bulk density,
high purity that allows a use as ligands in industrial scale processes.

In particular, the crystalline forms according to the invention are easier to handle than other known solid forms of 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepine, since they are obtained in the form of discrete crystals or crystallites or crystal agglomerates.

Subject of the present invention is also a composition comprising at least 50% by weight, based on the total weight of the composition, of at least one crystalline form of compound I according to the invention. Further components of the composition may be crystalline forms of compound I different from the crystalline forms of the invention, compound I in amorphous form and components different from compound I. Preferably, the composition comprises at least 75% by weight, more preferably at least 85% by weight, in particular at least 90% by weight, especially at least 95% by weight, based on the total weight of the composition, of at least one crystalline form of compound I according to the invention.

The composition of at least one crystalline form of compound I according to the invention comprises preferably at least 75% by weight, more preferably at least 85% by weight, in particular at least 90% by weight, especially at least 95% by weight, more especially at least 98% by weight, e.g. at least 99% by weight, of at least one crystalline form of compound I according to the invention, based on the total content of component I.

A further object of the invention relates to a composition of compound I that comprises at least two (i.e. 2, 3, 4 or 5) crystalline forms, selected from
 the toluene-monosolvate as defined herein,
 the non-solvated crystalline form as defined herein,
 the acetone-solvate "A" as defined herein,
 the acetone-solvate "B" as defined herein,
 the acetone-solvate "C" as defined herein.

In principle, the synthesis of 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepine (compound I) used as starting material for the preparation of the crystalline solvate and non-solvate forms of the invention, can be effected by known processes. Suitable processes are those for the synthesis of organic diphosphites that are described e.g. in EP 0 214 622 A2, U.S. Pat. Nos. 4,668,651, 4,748,261, 4,769,498, 4,885,401, 5,235,113, 5,391,801, 5,663,403, 5,728,861, 6,172,267, DE 103 60 771 A1, WO 2003/062171 and WO 2003/062251. The teaching of those documents is incorporated herein by reference.

In a suitable embodiment, compound I is prepared by a process, comprising the following steps:
a) reacting a first aromatic diol of formula (A1)

with PCl₃ to obtain the phosphoromonochloridite (A2)

b) reacting the phosphoromonochloridite (A2) with a second aromatic diol (A3)

to obtain compound I.

There are several methods to remove the halogen halides formed in the condensation reactions. Such methods are known to a person skilled in the art and described inter alia in the afore-mentioned documents. One possibility is the addition of an at least stoichiometric amount of a base. Typical bases employed to remove the halogen halides are nitrogen bases.

In a preferred embodiment, compound I is prepared by the method described in WO 2003/062171 and WO 2003/062251 (e.g. according to example 17). The teaching of these documents is incorporated herein by reference. According to this method the halogen halides formed in at least one of the condensation reactions are separated from the reaction mixture by means of an auxiliary base. Said base forms a salt with the halogen halides which is liquid at temperatures at which the valuable product is not significantly decomposed during separation and wherein the salt of the auxiliary base and the valuable product or the solution of the valuable product form two immiscible fluid phases.

Crystalline Toluene-Monosolvate of compound I

The crystalline toluene-monosolvate of compound I can be identified by X-ray powder diffractometry on the basis of its diffraction diagram. Thus, an X-ray powder diffractogram recorded at 25° C. using Cu—Kα radiation (1.54178 Å) displays at least 5, often at least 6, in particular at least 7, and especially all of the reflections stated in the following Table 1 as 2θ values, and as interplanar spacings d:

TABLE 1

| 2θ values | d [Å] |
|---|---|
| 5.15 ± 0.2° | 17.14 |
| 7.59 ± 0.2° | 11.65 |
| 8.56 ± 0.2° | 10.32 |
| 8.80 ± 0.2° | 10.04 |
| 8.97 ± 0.2° | 9.84 |
| 9.65 ± 0.2° | 9.15 |
| 10.55 ± 0.2° | 8.37 |
| 11.47 ± 0.2° | forme |
| 14.76 ± 0.2° | 5.99 |
| 15.35 ± 0.2° | 5.76 |

Studies on single crystals of the toluene-monosolvate of compound I show that the basic crystal structure is orthorhombic. The unit cell has the space group Pbca. The characteristic data of the crystal structure of the toluene-monosolvate of compound I (determined at −173° C.) are summarized in Table 2.

TABLE 2

| Crystallographic properties of the toluene-monosolvate of compound I | |
|---|---|
| Parameter | |
| Crystal system | Orthorhombic |
| Space group | P b c a |

TABLE 2-continued

Crystallographic properties of the
toluene-monosolvate of compound I

Figure 2:
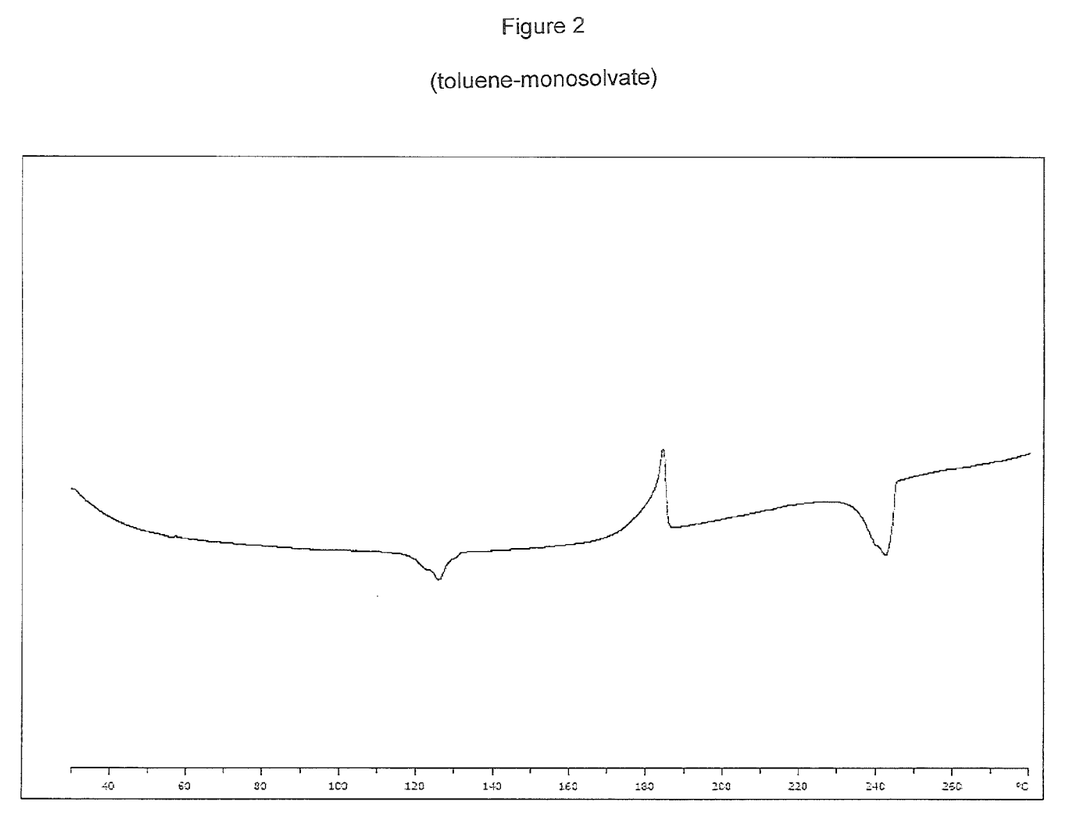
FIG. 2 shows the DSC of the crystalline toluene-monosolvate of compound I.

| Parameter | |
|---|---|
| a | 12.038(3) Å |
| b | 24.764(6) Å |
| c | 34.273(8) Å |
| α | 90° |
| β | 90° |
| γ | 90° |
| Volume | 10217.1 Å$^3$ |
| Z | 8 |
| R-Factor (%) | 3.89 | a, b, c = Length of the edges of the unit cell
α, β, γ = Angles of the unit cell
Z = Number of molecules, in the unit cell The toluene-monosolvate of compound I shows characteristic peaks in the differential scanning calorimetry (DSC) (see FIG. 2). At 126° C. desolvation occurs and the crystalline form is converted into an amorphous form. At 184° C. recrystallization is observed into the stable non-solvate form. A further peak at 243° C. can be attributed to the melting of the non-solvate form.

The preparation of the crystalline toluene-monosolvate of 6,6'-[[3,3',5,5'-tetrakis(1,1-dimethylethyl)-[1,1'-biphenyl]-2,2'-diyl]bis(oxy)]bis-dibenzo[d,f][1,3,2]-dioxa-phosphepine according to the invention is effected by crystallization from a toluene solution.

A further object of the invention is a process for the preparation of the crystalline toluene-monosolvate of compound I as described above, comprising:
i) preparing a solution of compound I in toluene which is supersaturated at a temperature of 30° C., and
ii) allowing compound I to crystallize at a temperature of not more than 30° C.

Preferably, in step i) a saturated solution of compound I at a temperature of at least 80° C. and ambient pressure is prepared. More preferably, in step i) a saturated solution of compound I at reflux temperature and ambient pressure is prepared. It is understood, that this solution will become supersaturated with compound I at lower temperatures, as long as no crystallisation of compound I takes place.

For the preparation of the solution by dissolution of compound I, essentially any known form of compound I can be used. Often amorphous 6,6'-[[3,3',5,5'-tetrakis(1,1-dimethylethyl)-[1,1'-biphenyl]-2,2'-diyl]bis(oxy)]bis-dibenzo[d,f][1,3,2]-dioxa-phosphepine or a mixture of different crystalline modifications or a mixture of amorphous and crystalline 6,6'-[[3,3',5,5'-Tetrakis(1,1-dimethylethyl)-[1,1'-biphenyl]-2,2'-diyl]bis(oxy)]bis-dibenzo[d,f][1,3,2]-dioxaphosphepine will be used.

According to a special embodiment, the solution of compound I can also be prepared by a chemical reaction that leads to a reaction mixture which comprises the compound I, if appropriate after removal of reagents and/or side-products. Here the procedure can be used of performing the reaction in toluene as the organic solvent or by transferring the reaction product into toluene as solvent by known methods.

It is of critical importance for the formation of the crystalline toluene-monosolvate of compound I that the crystallization in step ii) is performed at a temperature of not more than 30° C.

In a first preferred embodiment, the crystallization in step ii) is performed by cooling a solution of compound I in toluene to a temperature of not more than 30° C., wherein the solution has a concentration of compound I that it is supersaturated at a temperature of not more than 30° C. The formation of crystals at higher temperatures can be prevented e.g. by choosing a sufficiently high cooling rate and/or avoid the presence of seed crystals. If seed crystals of the crystalline toluene-monosolvate of compound I are employed, they are added at a temperature of not more than 30° C.

In a further preferred embodiment, the crystallization in step ii) is performed by adding the solution of compound I in toluene having a temperature of at least 80° C. to a vessel containing methanol having a temperature of not more than 30° C., and wherein during the addition and the crystallization the temperature of the solvent-mixture in the vessel is kept at a value of not more than 30° C. The temperature of the solvent-mixture in the vessel can be kept at a value of not more than 30° C. e.g. by at least one of the following measures:
using methanol of a sufficiently low initial temperature,
using a sufficiently large amount of methanol,
cooling the vessel during the addition and crystallization.

The crystallization of the crystalline toluene-monosolvate of 6,6'-[[3,3',5,5'-tetrakis(1,1-dimethylethyl)-[1,1'-biphenyl]-2,2'-diyl]bis(oxy)]bis-dibenzo[d,f][1,3,2]-dioxa-phosphepine can optionally be promoted or accelerated by seeding with seed crystals of the crystalline toluene-monosolvate of compound I. The seed crystals of the toluene-monosolvate of compound I are usually added before the crystallization.

If seed crystals are employed for the crystallization, the quantity thereof is preferably 0.001 to 10% by weight, more preferably 0.005 to 5% by weight, in particular 0.01 to 1% by weight and especially 0.05 to 0.5% by weight, based on the dissolved compound I.

The isolation of the crystalline toluene-monosolvate of compound I from the crystallization product, i.e. the separation of the toluene-monosolvate from the mother liquor, is achieved by normal techniques for the separation of solid components from liquids, e.g. by filtration, centrifugation or by decantation. In a suitable embodiment, the isolated solid will be washed, preferably with toluene. The washing is typically effected at temperatures below 30° C., often below 25° C. and in particular below 20° C., in order to keep the loss of valuable product as low as possible. Next, the crystalline toluene-monosolvate of compound I can be dried and then fed into further processing.

The content of crystalline toluene-monosolvate of compound I, based on the total quantity of compound I, is typically at least 90% and often at least 95% and especially at least 97%.

Non-Solvated Crystalline Form of Compound I

Surprisingly it has been found, that whereas at a sufficiently low-temperature it is possible to obtain the aforementioned toluene-solvate of compound I, at a higher temperature a stable non-solvated crystalline form of compound I can be isolated.

The non-solvated crystalline form of compound I can be identified by X-ray powder diffractometry on the basis of its diffraction diagram. Thus, an X-ray powder diffractogram recorded at 25° C. using Cu—Kα radiation (1.54178 Å) displays at least 5, often at least 6, in particular at least 7, and especially all of the reflections stated in the following Table 3 as 2θ values, and as interplanar spacings d:

TABLE 3

| 2θ values | d [Å] |
|---|---|
| 5.39 ± 0.2° | 16.39 |
| 7.04 ± 0.2° | 12.55 |

TABLE 3-continued

| 2θ values | d [Å] |
|---|---|
| 8.44 ± 0.2° | 10.46 |
| 8.65 ± 0.2° | 10.21 |
| 9.08 ± 0.2° | 9.74 |
| 9.66 ± 0.2° | 9.15 |
| 10.66 ± 0.2° | 8.29 |
| 12.60 ± 0.2° | 7.02 |
| 16.25 ± 0.2° | 5.45 |
| 17.36 ± 0.2° | 5.10 |

Studies on single crystals of the non-solvated form of compound I show that the basic crystal structure is monoclinic. The unit cell has the space group P 2$_1$/c. The characteristic data of the crystal structure of the non-solvated form of compound I (determined at −173° C.) are summarized in Table 4.

TABLE 4

| Crystallographic properties of the non-solvated form of compound I | |
|---|---|
| Parameter | |
| Crystal system | Monoclinic |
| Space group | P 2$_1$/c |
| a | 12.5665(4) Å |
| b | 11.0354(4) Å |
| c | 32.817(1) Å |
| α | 90° |
| β | 92815(1)° |
| γ | 90° |
| Volume | 4545.5 Å$^3$ |
| Z | 4 |
| R-Factor (%) | 5.67 | a, b, c = Length of the edges of the unit cell
α, β, γ = Angles of the unit cell
Z = Number of molecules, in the unit cell The non-solvate of compound I shows in the DSC a peak attributed to melting at 243° C.

A further object of the invention is a process for the preparation of the non-solvated crystalline form of compound I, wherein 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepine is allowed to crystallized at a temperature of above 65° C. or wherein 6,6'-[[3,3',5,5'-tetrakis(1,1-dimethylethyl)-[1,1'-biphenyl]-2,2'-diyl]bis(oxy)]bis-dibenzo[d,f][1,3,2]-dioxa-phosphepine is suspended in a solvent and the suspended material is agitated in the suspension at a temperature of at least 65° C.

In a preferred embodiment, the suspended material is agitated in the suspension at a temperature of at least 75° C., more preferably at least 85° C., especially at a temperature above the boiling point of toluene at ambient pressure.

Preferably, the solvent is selected from alkylbenzenes, arylalkylether, chlorbenzene and mixtures thereof. Preferably, the solvent is selected from solvents and mixtures of solvents having a boiling point of at least 100° C. at 1013 mbar.

Suitable solvents are e.g. toluene, di-n-butylether and mixtures thereof. A particularly preferred solvent comprises or consists of toluene.

Preferably, the suspension time is at least 10 minutes, more preferably at least 30 minutes, in particular at least 1 hour.

Preferably, the suspension is separated from the mother liquor at a temperature of at least 65° C., more preferably at least 75° C., in particular at least 85° C.

The isolation of suspended solid, i.e. the crystalline non-solvated form of compound I from the mother liquor can be performed by normal techniques for the separation of solid components from liquids, e.g. by filtration, centrifugation or by decantation. In a suitable embodiment, the isolated solid will be washed, preferably with toluene. The washing is typically effected at temperatures of at least 65° C. Next, the crystalline non-solvate form of compound I can be dried and then fed into further processing.

Crystalline Acetone-Solvate "A" of Compound I

The crystalline acetone-solvate "A" of compound I can be identified by X-ray powder diffractometry on the basis of its diffraction diagram. Thus, an X-ray powder diffractogram recorded at 25° C. using Cu—Kα radiation (1.54178 Å) displays at least 5, often at least 6, in particular at least 7, and especially all of the reflections stated in the following Table 5 as 2θ values, and as interplanar spacings d:

TABLE 5

| 2θ values | d [Å] |
|---|---|
| 6.67 ± 0.2° | 13.22 |
| 7.11 ± 0.2° | 12.43 |
| 7.87 ± 0.2° | 11.22 |
| 8.31 ± 0.2° | 10.63 |
| 8.96 ± 0.2° | 9.87 |
| 9.17 ± 0.2° | 9.64 |
| 10.68 ± 0.2° | 8.28 |
| 15.78 ± 0.2° | 5.61 |
| 16.10 ± 0.2° | 5.50 |
| 18.63 ± 0.2° | 4.76 |

Studies on single crystals of the acetone-solvate "A" of compound I show that the basic crystal structure is monoclinic. The unit cell has the space group P2$_1$/n. The characteristic data of the crystal structure of the acetone-solvate "A" of compound I (determined at −173° C.) are summarized in Table 6.

TABLE 6

| Crystallographic properties of the acetone-solvate "A" of compound I | |
|---|---|
| Parameter | |
| Crystal system | Monoclinic |
| Space group | P2$_1$/n |
| a | 12.755(2) Å |
| b | 26.444(5) Å |
| c | 14.490(3) Å |
| α | 90° |
| β | 103655(8)° |
| γ | 90° |
| Volume | 4749.24 Å$^3$ |
| Z | 4 |
| R-Factor (%) | 6.6 | a, b, c = Length of the edges of the unit cell
α, β, γ = Angles of the unit cell
Z = Number of molecules, in the unit cell A further object of the invention is a process for the preparation of the crystalline acetone-solvate "A" of compound I as defined before, comprising:

I) preparing a suspension of compound I in acetone,
II) heating the suspension to bring compound I into solution, and
III) cooling the solution obtained in step II) and performing a crystallization.

Preferably, in step I) the suspension of compound I in acetone is prepared at a temperature of from 10 to 30° C.

Preferably in step II) the suspension is heated to a temperature of at least 50° C., preferably to reflux temperature. The heating is preferably performed at ambient pressure. Acetone has a boiling point of 56° C. at atmospheric pressure (101.3 kPa).

Preferably, in step III) the solution obtained in step II) is cooled to a temperature of from reflux temperature (about 56°) to ambient temperature (about 20° C.).

For the preparation of the solution of compound I, essentially any known form of compound I can be used. Often amorphous 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepine or a mixture of different crystalline modifications or a mixture of amorphous and crystalline 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepine will be used.

The isolation of the crystalline acetone-solvate A of compound I from the mother liquor, is achieved by normal techniques for the separation of solid components from liquids, e.g. by filtration, centrifugation or by decantation. In a suitable embodiment, the isolated acetone-solvate A will be washed, preferably with acetone. The washing is typically effected at temperatures below 30° C., often below 25° C. and in particular below 20° C., in order to keep the loss of valuable product as low as possible.

The content of crystalline acetone-solvate A of compound I, based on the total quantity of compound I is typically at least 90% and often at least 95% and especially at least 97%.

Crystalline Acetone-Solvate "B" of Compound I

The crystalline acetone-solvate "B" of compound I can be identified by X-ray powder diffractometry on the basis of its diffraction diagram. Thus, an X-ray powder diffractogram recorded at 25° C. using Cu—Kα radiation (1.54178 Å) displays at least 5, often at least 6, in particular at least 7, and especially all of the reflections stated in the following Table 7 as 2θ values, and as interplanar spacings d:

TABLE 7

| 2θ values | d [Å] |
|---|---|
| 8.13 ± 0.2° | 10.87 |
| 8.70 ± 0.2° | 10.16 |
| 8.95 ± 0.2° | 9.87 |
| 10.02 ± 0.2° | 8.82 |
| 10.98 ± 0.2° | 8.05 |
| 11.71 ± 0.2° | 7.55 |
| 14.16 ± 0.2° | 6.25 |
| 15.65 ± 0.2° | 5.66 |
| 16.98 ± 0.2° | 5.21 |
| 18.08 ± 0.2° | 4.90 |

Studies on single crystals of the acetone-solvate "B" of compound I show that the basic crystal structure is monoclinic. The unit cell has the space group $P2_1/c$. The characteristic data of the crystal structure of the acetone-solvate "B" of compound I (determined at −173° C.) are summarized in Table 8.

TABLE 8

Crystallographic properties of the acetone-solvate "B" of compound I

| Parameter | |
|---|---|
| Crystal system | Monoclinic |
| Space group | $P2_1/c$ |
| a | 19.597(6) Å |
| b | 11.849(4) Å |
| c | 21.936(7) Å |
| α | 90° |
| β | 115.87(1)° |
| γ | 90° |
| Volume | 4583.4 Å$^3$ |
| Z | 4 |
| R-Factor (%) | 5.4 | a, b, c = Length of the edges of the unit cell
α, β, γ = Angles of the unit cell
Z = Number of molecules, in the unit cell A further object of the invention is a process for the preparation of the crystalline acetone-solvate "B" of compound I as defined before, comprising:

I) providing a solution of compound I in acetone,
II) allowing a part of the solvent of the solution provided in step I to evaporate and thus inducing crystallization.

Preferably, in step I) the solution of compound I in acetone is provided at a temperature of from 40 to 20° C. In particular the solution of compound I in acetone is provided at ambient temperature.

The solution of compound I can for example be prepared by dissolution of compound I in acetone.

Preferably in step II) the solution is cooled to a temperature of at most 15° C., preferably at most 10° C.

The isolation of the crystalline acetone-solvate "B" of compound I from the mother liquor is achieved by normal techniques for the separation of solid components from liquids, e.g. by filtration, centrifugation or by decantation. In a suitable embodiment, the isolated solid will be washed, preferably with acetone. The washing is typically effected at temperatures below 30° C., often below 25° C. and in particular below 20° C., in order to keep the loss of valuable product as low as possible.

The content of crystalline acetone-solvate "B" of compound I, based on the total quantity of compound I is typically at least 90% and often at least 95% and especially at least 97%.

Crystalline Acetone-Solvate "C" of Compound I

The crystalline acetone-solvate "C" of compound I can be identified by X-ray powder diffractometry on the basis of its diffraction diagram. Thus, an X-ray powder diffractogram recorded at 25° C. using Cu—Kα radiation (1.54178 Å) displays at least 5, often at least 6, in particular at least 7, and especially all of the reflections stated in the following Table 9 as 2θ values, and as interplanar spacings d:

TABLE 9

| 2θ values | d [Å] |
|---|---|
| 5.40 ± 0.2° | 16.34 |
| 6.97 ± 0.2° | 12.67 |
| 7.64 ± 0.2° | 11.56 |
| 8.39 ± 0.2° | 10.53 |
| 9.24 ± 0.2° | 9.56 |
| 9.44 ± 0.2° | 9.35 |
| 11.23 ± 0.2° | 7.87 |
| 13.46 ± 0.2° | 6.57 |
| 15.32 ± 0.2° | 5.78 |
| 18.35 ± 0.2° | 4.83 |

Studies on single crystals of the acetone-solvate "C" of compound I show that the basic crystal structure is triclinic. The unit cell has the space group P-1. The characteristic data of the crystal structure of the acetone-solvate "C" of compound I (determined at −173° C.) are summarized in Table 8.

TABLE 10

Crystallographic properties of the acetone-solvate "C" of compound I

| Parameter | |
| --- | --- |
| Crystal system | Triclinic |
| Space group | P-1 |
| a | 11.5679(3) Å |
| b | 12.7377(3) Å |
| c | 16.4185(8) Å |
| α | 95.632(1)° |
| β | 90.723(1)° |
| γ | 92.197(5)° |
| Volume | 2405.5 Å$^3$ |
| Z | 2 |
| R-Factor (%) | 3.6 | a, b, c = Length of the edges of the unit cell
α, β, γ = Angles of the unit cell
Z = Number of molecules, in the unit cell A further object of the invention is a method to obtain the crystalline acetone-solvate "C" of compound I as defined before, comprising:

I) preparing at a temperature of from about 15 to 25° C. a saturated solution of compound I in acetone,
II) warming the solution obtained in step I) to a temperature that is about 15 to 25° C. higher than the temperature in step I),
III) allowing the warmed solution obtained in step II) to cool to a temperature that is about 5 to 15° C. below the temperature of step I), wherein steps I) to III) are repeated for at least 10 times.

Preferably, in step I) the saturated solution of compound I in acetone is prepared at ambient temperature.

Preferably, in step II) the solution is warmed to a temperature that is about 20° C. higher than the temperature in step I).

Preferably, in step III) the solution is allowed to cool to a temperature that is about 5 to 15° C. below the temperature of step I).

Preferably, steps I) to III) are repeated 10 to 15 times, more preferably 10 times.

The isolation of the crystalline acetone-solvate "C" of compound I from the mother liquor is achieved by normal techniques for the separation of solid components from liquids, e.g. by filtration, centrifugation or by decantation. In a suitable embodiment, the isolated acetone-solvate "C" will be washed, preferably with acetone. The washing is typically effected at temperatures below 30° C., often below 25° C. and in particular below 20° C., in order to keep the loss of valuable product as low as possible.

The content of crystalline acetone-solvate "C" of compound I, based on the total quantity of compound I is typically at least 90% and often at least 95% and especially at least 97%.

The crystalline solvate and non-solvate forms of 6,6'-[[3,3',5,5'-tetrakis(1,1-dimethylethyl)-[1,1'-biphenyl]-2,2'-diyl]bis(oxy)]bis-dibenzo[d,f][1,3,2]-dioxa-phosphepine according to the invention are especially suitable as ligands of a transition metal catalyst for a hydroformylation, hydrocyanation or hydrogenation.

As mentioned before, the crystalline forms of compound I according to the invention, including the solvates of compound I, and compositions thereof comprising a major amount of those crystalline forms have advantageous properties, in particular the following properties:

a low tackiness,
low tendency to cake,
low tendency of forming dust,
a high bulk density and
a high purity of the compound I.

Surprisingly, it was also found that crystalline forms of the invention containing solvent in the crystal lattice can be employed as ligands for transition metal catalysts without an adverse effect of the solvent on the formation of homogeneous catalysts and/or the catalyzed reaction.

The crystalline forms of the invention are also characterized by a good flowability.

The low tendency to cake allows that the crystalline forms of the invention can be stored even over longer periods of time prior to their use. Advantageously a mechanical disintegration prior to use is in many cases not necessary.

The crystalline forms of the invention allow easier handling, e.g. weighing, filling and metering procedures, in that the formation of dust, which might be hazardous to health upon inhalation or contact with skin or eyes is minimized.

As a result of these properties, the crystalline forms of the invention are in particular suitable for the manufacture of transition metal catalysts.

In contrast to acetonitrile contained in acetonitrile-solvates of compound I, toluene and acetone contained in the toluene- or acetone-solvates of compound I under conditions of homogeneous catalysis do not interact with catalytically active metal centres of the transition metal catalysts formed from a transition metal and compound I and hence do not interfere with the transition metal catalysis, e.g. by reducing catalytic activity or selectivity.

A further object of the invention is the use of a crystalline form of compound I as defined above for the production of a transition metal catalyst for hydroformylation, hydrocyanation or hydrogenation.

A further object of the invention is a method for producing a transition metal catalyst, wherein a crystalline form of compound I as defined above is provided and brought into contact with a compound or a complex of a transition metal in an inert solvent.

A further object of the invention is a transition metal catalyst, obtainable by a method wherein a crystalline form of compound I, as defined above and in the following, is provided and brought into contact with a compound or a complex of a transition metal in an inert solvent.

The following statements apply equally to the catalysts of the invention as well as the method for their production and their use.

Preferably, the catalyst of the invention is prepared from 6,6'-[[3,3',5,5'-tetrakis(1,1-dimethylethyl)-[1,1'-biphenyl]-2,2'-diyl]bis(oxy)]bis-dibenzo[d,f][1,3,2]-dioxa-phosphepine, which is composed of at least 50% by weight, more preferably at least 75% by weight, in particular at least 90% by weight, of at least one crystalline form, selected from the solvate and non-solvate forms of 6,6'-[[3,3',5,5'-tetrakis(1,1-dimethylethyl)-[1,1'-biphenyl]-2,2'-diyl]bis(oxy)]bis-dibenzo[d,f][1,3,2]-dioxa-phosphepine according to the invention and mixtures thereof.

In a first embodiment, the catalyst comprises the crystalline toluene-monosolvate of compound I as ligand. Then, preferably the catalyst comprises at least 50% by weight, more preferably at least 75% by weight, in particular at least 90% by weight, of the crystalline toluene-monosolvate of compound I, based on the total weight of compound I employed as ligand.

In a second embodiment, the catalyst comprises the crystalline non-solvated form of compound I as ligand. Then, preferably the catalyst comprises at least 50% by weight, more preferably at least 75% by weight, in particular at least 90% by weight, of the crystalline non-solvated form of compound I, based on the total weight of compound I employed as ligand.

In a third embodiment, the catalyst comprises the crystalline acetone-solvate "A" of compound I as ligand. Then, preferably the catalyst comprises at least 50% by weight, more preferably at least 75% by weight, in particular at least 90% by weight, of the crystalline acetone-solvate "A" of compound I, based on the total weight of compound I employed as ligand.

In a fourth embodiment, the catalyst comprises the crystalline acetone-solvate "B" of compound I as ligand. Then, preferably the catalyst comprises at least 50% by weight, more preferably at least 75% by weight, in particular at least 90% by weight, of the crystalline acetone-solvate "B" of compound I, based on the total weight of compound I employed as ligand.

In a fifth embodiment, the catalyst comprises the crystalline acetone-solvate "C" of compound I as ligand. Then, preferably the catalyst comprises at least 50% by weight, more preferably at least 75% by weight, in particular at least 90% by weight, of the crystalline acetone-solvate "C" of compound I, based on the total weight of compound I employed as ligand.

In general, the metal concentration in the reaction medium is in the range from about 1 to 10 000 ppm. The molar ratio of ligand to transition metal is generally in the range from about 0.5:1 to 1000:1, preferably from 1:1 to 500:1.

A person skilled in the art will choose the transition metal depending on the reaction to be catalyzed. The transition metal is preferably a metal of groups 8, 9 or 10 of the periodic table of the elements, preferably from metals of the groups 9 and 10 (i.e. Co, Ni, Rh, Pd, Ir, Pt).

In addition to the above-described ligands, the catalysts of the invention can have at least one further ligand which is preferably selected from among, carboxylates, acetylacetonate, arylsulfonates and alkylsulfonates, hydride, CO, olefins, dienes, cycloolefins, such as cyclooctadiene and norbornadiene, nitriles, aromatics and heteroaromatics, ethers, and monodentate, bidentate and polydentate phosphoramidite and phosphite ligands. Especially, the further ligands are selected from hydride, CO and olefins (i.e. species that are capable of forming the active catalyst under the hydroformylation reaction).

The catalysts of the invention (or prepared by the method of the invention or produced by using a crystalline form of compound I according to the invention) are particularly suitable as catalyst for a hydroformylation reaction. A further object of the invention is a process for hydroformylating compounds which contain at least one ethylenically unsaturated double bond by reacting with carbon monoxide and hydrogen in the presence of a catalyst comprising at least one complex of a metal, selected from cobalt or rhodium. Particular preference is given to using rhodium.

In a preferred embodiment, the hydroformylation catalysts are prepared in situ, in the reactor used for the hydroformylation reaction. However, the catalysts according to the invention may, if desired, also be prepared separately and be isolated by customary processes. To prepare the catalysts according to the invention in situ, for example, at least one crystalline form of compound I according to the invention, a compound or a complex of a transistion metal, optionally at least one further additional ligand and optionally an activator may be reacted in an inert solvent under the hydroformylation conditions.

Suitable rhodium compounds or complexes for the preparation of the hydroformylation catalysts are, for example, rhodium(II) and rhodium(III) salts such as rhodium(II) or rhodium(III) carboxylate, rhodium(II) and rhodium(III) acetate, etc. Also suitable are rhodium complexes such as rhodium bis(carbonyl)acetylacetonate, acetylacetonatobis-ethylenerhodium(I), acetylacetonato cyclooctadienyl rhodium(I), acetylacetonato norbornadienyl rhodium(I), acetylacetonato carbonyl triphenylphosphin rhodium(I) etc.

Suitable cobalt compounds for the preparation of the hydroformylation catalysts are, for example, cobalt(II) sulfate, cobalt(II) carbonate, their amine or hydrate complexes, cobalt carboxylates such as cobalt acetate, cobalt ethylhexanoate, cobalt naphthanoate, and also the cobalt caproate complex. The carbonyl complexes of cobalt such as dicobalt octacarbonyl, tetracobalt dodecacarbonyl and hexacobalt hexadecacarbonyl may also be used here.

The compounds of cobalt or rhodium which have been mentioned and are further suitable compounds are known in principle and adequately described in the literature, or may be prepared by those skilled in the art in a similar manner to the compounds already known.

For the hydroformylation and/or the work-up of the catalyst measures can be taken that enhance the catalytic activity and/or prevent a decomposition of the catalyst. Such methods are described inter alia in EP 0 590 613, EP 0 865 418, EP 0 874 796, EP 0 874 797, EP 0 876 321, EP 0 876 322, EP 0 904 259, EP 1 019 352, EP 1 019 353. The teaching of those documents is incorporated herein by reference.

The solvents are preferably the aldehydes which are formed in the hydroformylation of the particular olefins, and also their higher-boiling subsequent reaction products, for example the products of the aldol condensation. Solvents which are likewise suitable are aromatics such as toluene and xylenes, hydrocarbons or mixtures of hydrocarbons, also for diluting the abovementioned aldehydes and the subsequent products of the aldehydes. Further solvents are esters of aliphatic carboxylic acids with alkanols, for example Texanol™ and esters of aromatic carboxylic acids, e.g. $C_8$-$C_{13}$-dialkyl phthalates.

With regard to the preparation and use of hydroformylation catalysts, and their use in the homogeneous catalysis reference is made e.g. to EP 0 214 622 A2, U.S. Pat. No. 4,668,651, U.S. Pat. No. 4,748,261, 4,769,498, 4,885,401, 5,235,113, 5,391,801, 5,663,403, 5,728,861, 6,172,267, DE 103 60 771 A1, WO 2003/062171 and WO 2003/062251.

Useful substrates for the hydroformylation process according to the invention are in principle all compounds which contain one or more ethylenically unsaturated double bonds. These include, for example, olefins such as α-olefins, internal straight-chain and internal branched olefins, cyclic olefins and olefins with substituents that are essentially inert under the hydroformylation conditions. Preferred are olefin feeds comprising olefins having 2 to 12, in particular 3 to 8 carbon atoms.

Suitable α-olefins are, for example, ethylene, propene, 1-butene, 1-pentene, 1-hexene, 1-heptene, 1-octene, 1-nonene, 1-decene, 1-undecene, 1-dodecene, etc. Preferred branched, internal olefins are $C_4$-$C_{20}$-olefins such as 2-methyl-2-butene, 2-methyl-2-pentene, 3-methyl-2-pentene, branched, internal heptene mixtures, branched, internal octene mixtures, branched, internal nonene mixtures, branched, internal decene mixtures, branched, internal undecene mixtures, branched, internal dodecene mixtures, etc. Further olefins suitable for hydroformylation are $C_5$-$C_8$-cycloalkenes such as cyclopentene, cyclohexene, cycloheptene, cyclooctene and their derivatives, e.g. their $C_1$-$C_{20}$-alkyl derivatives having from 1 to 5 alkyl substituents. Further olefins suitable for hydroformylation are vinylaromatics such as styrene, α-methylstyrene, 4-isobutylstyrene, etc. Other olefins suitable for hydroformylation are the esters and amides of α,β-ethylenically unsaturated monocarboxylic and/or dicarboxylic acids, e.g. methyl 3-pentenoate, methyl 4-pentenoate, methyl oleate, methyl acrylate, methyl methacrylate, unsaturated nitriles such as 3-pentenenitrile, 4-pentenenitrile, acrylonitrile, vinyl ethers such as vinyl methyl ether, vinyl ethyl ether, vinyl propyl ether, etc., $C_1$-$C_{20}$-alkenols, $C_1$-$C_{20}$-alkenediols and alkadienols such as 2,7-octadien-1-ol. Further suitable substrates are dienes or polyenes having isolated or conjugated double bonds. These include, for example, 1,3-butadiene, 1,4-pentadiene, 1,5-hexadiene, 1,6-heptadiene, 1,7-octadiene, vinylcyclohexene, dicyclopentadiene, 1,5,9-cyclooctatriene and also homopolymers and copolymers of butadiene.

In a preferred embodiment, an industrially available olefin mixture is employed in the hydroformylation. Suitable are e.g. olefin mixtures that result from hydrocarbon cracking in petroleum processing, for example from catalytic cracking such as fluid catalytic cracking (FCC), thermal cracking or hydrocracking with subsequent dehydrogenation.

A preferred industrial olefin mixture is the $C_3$ fraction. The propylene feed which is suitable as starting material for the process of the present invention may comprise a proportion of propane in addition to propylene. It contains, for example, from 0.5 to 40% by weight, preferably from 2 to 30% by weight and in particular from 3 to 10% by weight, of propane. A preferred example is "chemical grade propylene" which contains from 3 to 10% by weight of propane. It is obtained, for example, by reaction of naphtha or natural gas in a steam cracker and subsequent work-up by distillation. A further example of a suitable propylene feed is "refinery grade propylene" which has propane contents of from 20 to 30%.

A further preferred industrial olefin mixture is the $C_4$ fraction. The $C_4$ fractions can be obtained, for example, by fluid catalytic cracking or steam cracking of gas oil or by steam cracking of naphtha. Depending on the composition of the $C_4$ fraction, a distinction is made between the total $C_4$ fraction (crude $C_4$ fraction), the raffinate I obtained after removal of 1,3-butadiene and the raffinate II obtained after removal of isobutene. Raffinate II is particularly preferred.

A further object of the invention is the use of a transition metal catalyst comprising as a ligand a crystalline form of compound I for a hydrocyanation.

The catalysts used for the hydrocyanation, too, comprise complexes of a metal of transition group VIII, in particular nickel, ruthenium, rhodium, palladium, platinum, preferably nickel, palladium or platinum and very particularly preferably nickel. The preparation of the metal complexes can be carried out as described above. The same applies to the in-situ preparation of the hydrocyanation catalysts of the invention.

Hydrocyanation processes are described in J. March, Advanced Organic Chemistry, 4th edition, pp. 811-812, which is hereby incorporated by reference.

With regard to the preparation and use of hydrocyanation catalysts, and their use in the homogeneous catalysis reference is made e.g. to U.S. Pat. No. 6,127,567.

A further object of the invention is the use of a transition metal catalyst comprising as a ligand a crystalline form of compound I for a hydrogenation.

The catalysts according to the invention used for hydrogenation preferably comprise at least one metal of group 9 or 10 of the Periodic Table of the Elements, i.e. a metal selected from among Rh, Ir, Ni, Co, Pd and Pt.

The amount of catalyst to be used depends, inter alia, on the respective catalytically active metal and on the form in which it is used and can be determined for the individual case by a person skilled in the art. Thus, for example, a Ni- or Co-comprising hydrogenation catalyst is used in an amount of preferably from 0.1 to 70% by weight, particularly preferably from 0.5 to 20% by weight and in particular from 1 to 10% by weight, based on the weight of the compound to be hydrogenated. The amount of catalyst indicated is based on the amount of active metal, i.e. on the catalytically active component of the catalyst. When noble metal catalysts comprising, for example, rhodium, ruthenium, platinum or palladium are used, they are used in amounts which are a factor of about 10 smaller.

The hydrogenation is preferably carried out at a temperature in the range from 0 to 250° C., particularly preferably in the range from 20 to 200° C. and in particular in the range from 50 to 150° C.

The reaction pressure in the hydrogenation reaction is preferably in the range from 1 to 300 bar, particularly preferably in the range from 50 to 250 bar and in particular in the range from 150 to 230 bar.

Both reaction pressure and reaction temperature depend, inter alia, on the activity and amount of the hydrogenation catalyst used and can be determined in the individual case by a person skilled in the art.

The hydrogenation can be carried out in a suitable solvent or in bulk. Suitable solvents are ones which are inert under the reaction conditions, i.e. neither react with the starting material or product nor themselves become changed, and can be separated off without problems from the isoalkanes obtained. Suitable solvents include, for example, open-chain and cyclic ethers, e.g. diethyl ether, methyl tert-butyl ether, tetrahydrofuran or 1,4-dioxane and alcohols, in particular $C_1$-$C_3$-alkanols such as methanol, ethanol, n-propanol or isopropanol. Mixtures of the abovementioned solvents are also suitable.

The hydrogen necessary for the hydrogenation can be used either in pure form or in the form of hydrogen-comprising gas mixtures. However, the latter must not comprise interfering amounts of catalyst poisons such as sulfur-comprising compounds or CO.

Examples of suitable hydrogen-comprising gas mixtures are those from the reforming process. However, preference is given to using hydrogen in pure form.

The hydrogenation can be carried out either continuously or batchwise.

The hydrogenation is generally carried out by initially charging the compound to be hydrogenated, if appropriate in a solvent. This reaction solution is then preferably admixed with the hydrogenation catalyst before hydrogen is introduced. Depending on the hydrogenation catalyst used, the hydrogenation is carried out at elevated temperature and/or superatmospheric pressure. When the reaction is carried out under pressure, it is possible to use the customary pressure vessels known from the prior art, e.g. autoclaves, stirring autoclaves and pressure reactors. If the hydrogenation is not carried out under a superatmospheric pressure of hydrogen, the customary reaction apparatuses of the prior art which are suitable for atmospheric pressure are possible. Examples are conventional stirred vessels which are preferably equipped with evaporative cooling, suitable mixers, introduction facilities, if appropriate heat exchanger elements and facilities for making the interior inert. In the case of a continuous reaction, the hydrogenation can be carried out under atmospheric pressure in reaction vessels, tube reactors, fixed-bed reactors and the like which are customary for this purpose.

The following figures and examples serve to illustrate the invention and should not be interpreted as limiting.

EXAMPLES

The X-ray powder diffractograms were recorded with a Panalytical X'Pert Pro diffractometer (manufacturer: Panalytical) in reflection geometry in the range from 2θ=3° to 35° with increments of 0.0167° using Cu—K$_\alpha$ radiation (1.54178 Å) at 25° C. The recorded 2θ values were used to calculate the stated interplanar spacings d. The intensity of the peaks (y-axis: linear intensity counts) is plotted versus the 2θ angle (x-axis in degrees 2θ).

The single crystal X-ray diffraction data were collected at 100 K on a Bruker AXS SMART 6000 CCD detector using Cu—Kα radiation from either a rotating anode or a microsource, both equipped with multi-layer mirrors. The structures were solved using dual space recycling methods and refined against F$^2$ with the SHELX TL software package (Bruker AXS, 2003). A multi-scan correction for systematic errors was applied using SADABS (G. M. Sheldrick, University of Göttingen, 2010).

DSC (differential scanning calorimetry) was performed on a Mettler Toledo DSC 822e module. The sample was placed in crimped but vented aluminium pans (sample size was 10 mg). The thermal behavior was analyzed in the range of 30 to 280° C. by using a heating rate of 5° C./min and a stream of nitrogen flowing at 150 ml/during the experiment.

Melting points values and polymorphic transitions were confirmed by a Mettler Hot Stage in combination with a light microscope.

Example 1

Preparation of the Toluene-Monosolvate of Compound I

In a stirred three-necked flask with condenser and nitrogen inlet 30 g of 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepine was suspended in 50 ml of toluene at ambient temperature and heated in an oil bath for 3 h to reflux temperature (oil bath temperature: 120° C.). The obtained saturated solution was filtered hot and the filtrate was then cooled to a temperature of about 25° C. After standing over night, the formed crystals were filtered off, and dried in vacuo at 30° C. for 13 h.

Figure 1:
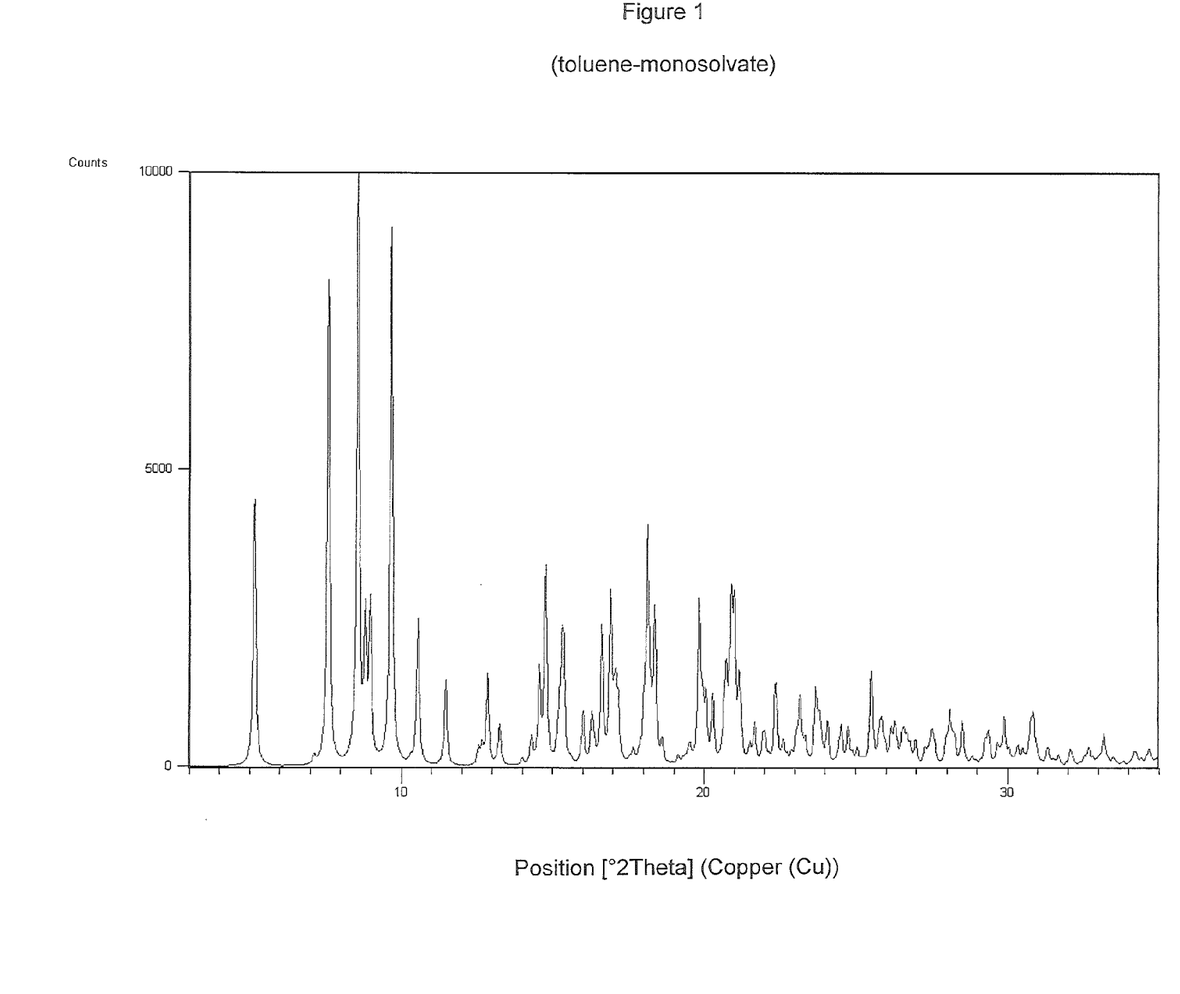
FIG. 1 shows an X-ray powder diffractogram of the crystalline toluene-monosolvate of 6,6'-[[3,3',5,5'-Tetrakis(1,1-dimethylethyl)-[1,1'-biphenyl]-2,2'-diyl]bis(oxy)]bis-dibenzo[d,f][1,3,2]-dioxaphosphepine (compound I). The X-ray powder diffractogram was recorded under the conditions stated in the following.

The crystallization product exhibited the X-ray powder diffractogram shown in FIG. 1 and the DSC shown in FIG. 2. After desolvation (peak at 126° C.) the amorphous form is obtained. By heating, the amorphous crystallizes into the stable non-solvate (recrystallization peak at 184° C.) that melts at 243° C.

Example 2

Preparation of the Non-Solvated Form of Compound I

In a stirred three-necked flask with condenser and nitrogen inlet 50.41 g of 6,6'-[[3,3',5,5'-Tetrakis(1,1-dimethylethyl)-[1,1'-biphenyl]-2,2'-diyl]bis(oxy)]bis-dibenzo[d,f][1,3,2]-dioxaphosphepine were suspended in 30.67 g of toluene at ambient temperature and heated in an oil bath for 3 h at reflux temperature (oil bath temperature: 120° C.). The hot crystal-containing mixture was passed through a suction filter which was heated to about 80° C. The obtained crystals were then cooled to ambient temperature, and dried in vacuo at 30° C. for 20 h.

Figure 3:
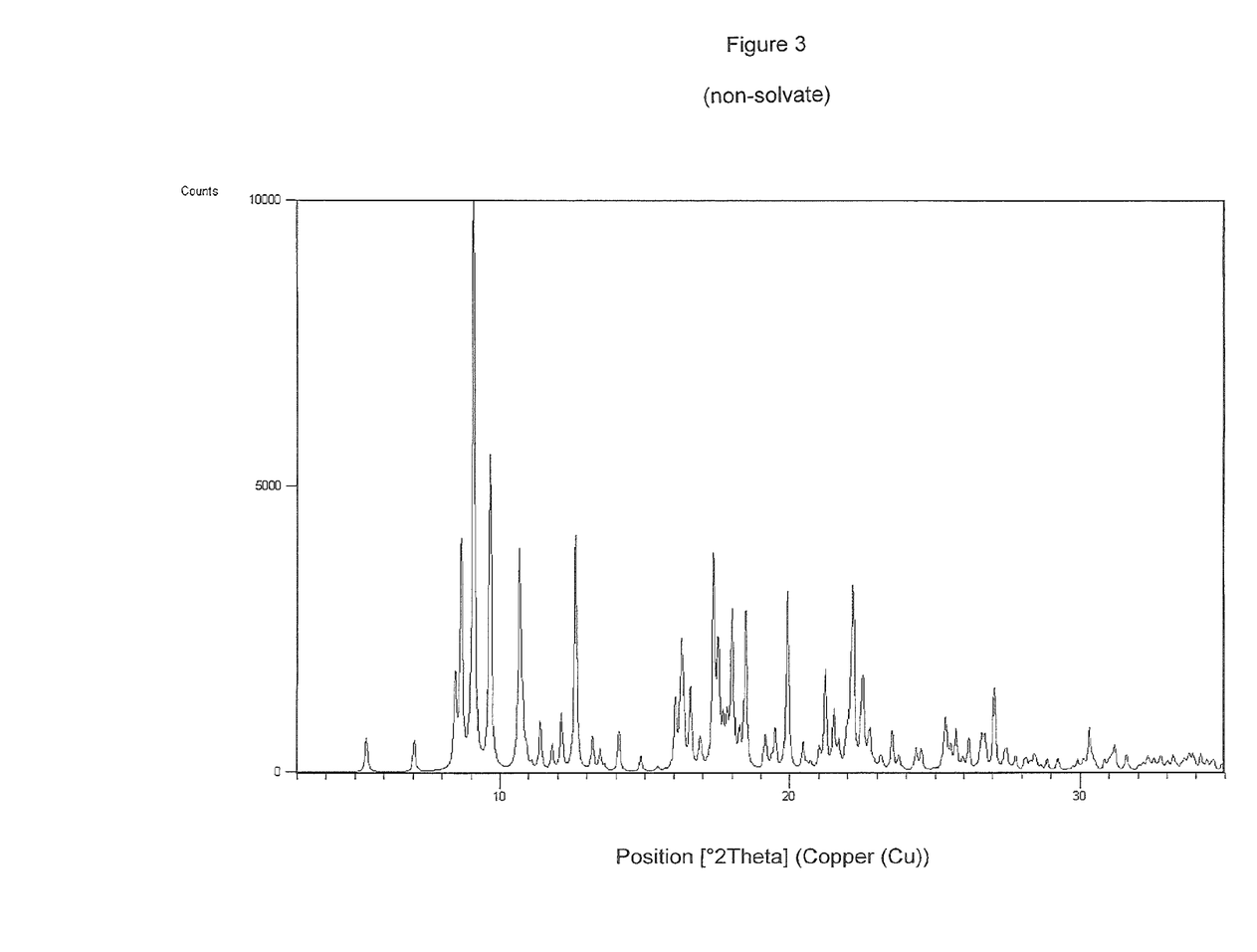
FIG. 3 shows an X-ray powder diffractogram of the non-solvated crystalline form of compound I. The X-ray powder diffractogram was recorded under the conditions stated in the following.

The crystallization product exhibited the X-ray powder diffractogram shown in FIG. 3.

Example 3

Preparation of the Acetone-Solvate "A" of Compound I

In a stirred 500 ml four three-necked flask with condenser, cooler and argon nitrogen inlet 20 g of 6,6'-[[3,3',5,5'-tetrakis(1,1-dimethylethyl)-[1,1'-biphenyl]-2,2'-diyl]bis(oxy)]-bis-dibenzo[d,f][1,3,2]-dioxaphosphepine whereas suspended in 300 g ml of acetone at ambient temperature and heated in an oil bath for 3 h at reflux temperature (oil bath temperature: 70° C.). The obtained solution was filtered whilst hot and the filtrate was then allowed to cool to ambient temperature. After stirring over night, the crystallized product was separated, dried in vacuo (0.15 mbar) at 30° C. for 2 h and analyzed.

Figure 4:
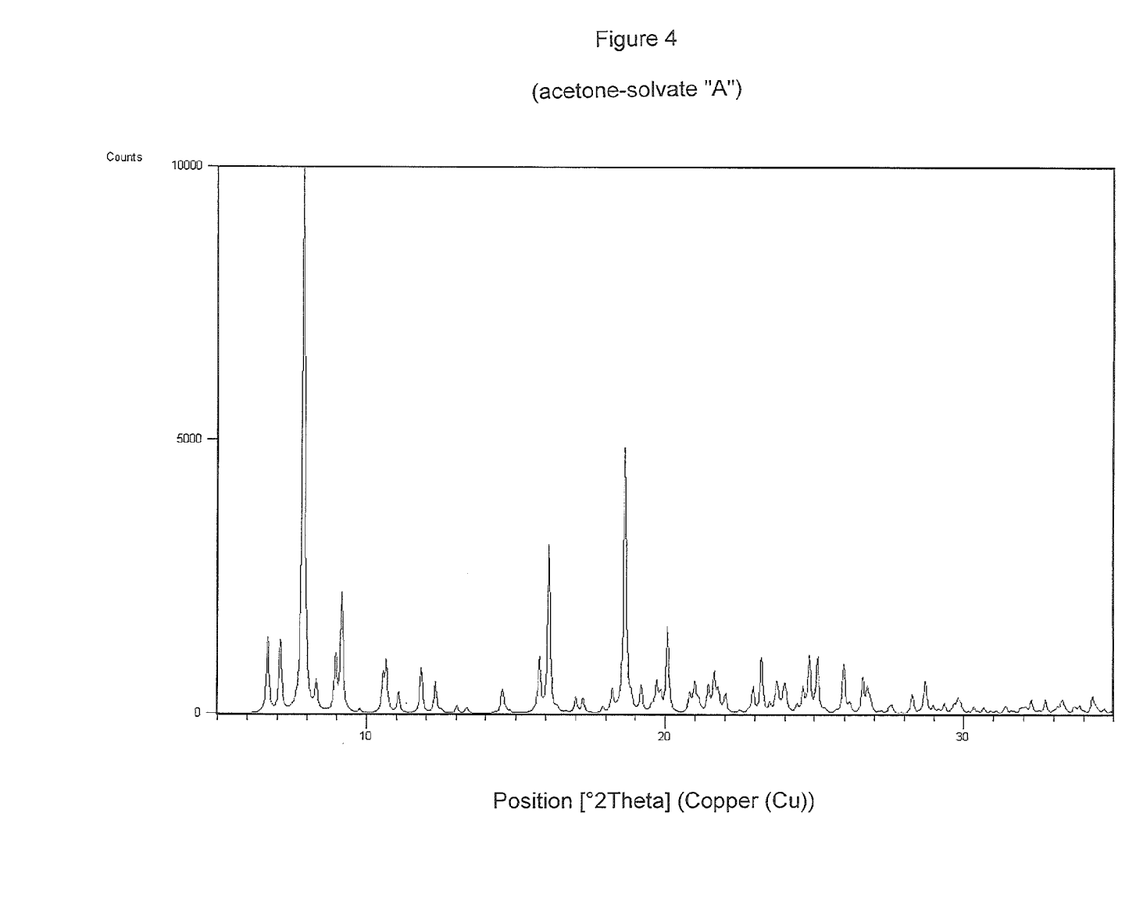
FIG. 4 shows an X-ray powder diffractogram of the crystalline acetone-solvate "A" of compound I. The X-ray powder diffractogram was recorded under the conditions stated in the following.

The crystallization product exhibited the X-ray powder diffractogram shown in FIG. 4.

Cell: P 2$_1$/n, Z=4, Z'=1; a=12.755(2) Å, b=26.444(5) Å, c=14.490(3) Å; α=90.00, β=103.655(8) γ=90.00; V=4749.24 Å$^3$, R-factor=6.6%.

Example 4

Preparation of the Acetone-Solvate "B" of Compound I

A vial was charged with 0.5 ml Aceton and ca. 2 mg of 6,6'-[[3,3',5,5'-tetrakis(1,1-dimethylethyl)-[1,1'-biphenyl]-2,2'-diyl]bis(oxy)]-bis-dibenzo[d,f][1,3,2]-dioxa-phosphepine. The clear solution was slowly evaporated at 5° C. in a refrigerator over several days. After a few days crystal formation was observed in the solution. Then a suitable crystal was isolated under the microscope and subjected to X-ray structure elucidation.

Cell: monoclinic P21/c, Z=4, Z'=1; a=19.597(6) Å, b=11.849(4) Å, c=21.936(7) Å; α=90.00, p=115.865°(14), γ=90.00; V=4583(3) Å$^3$, R-factor 5.4%.

Figure 5:
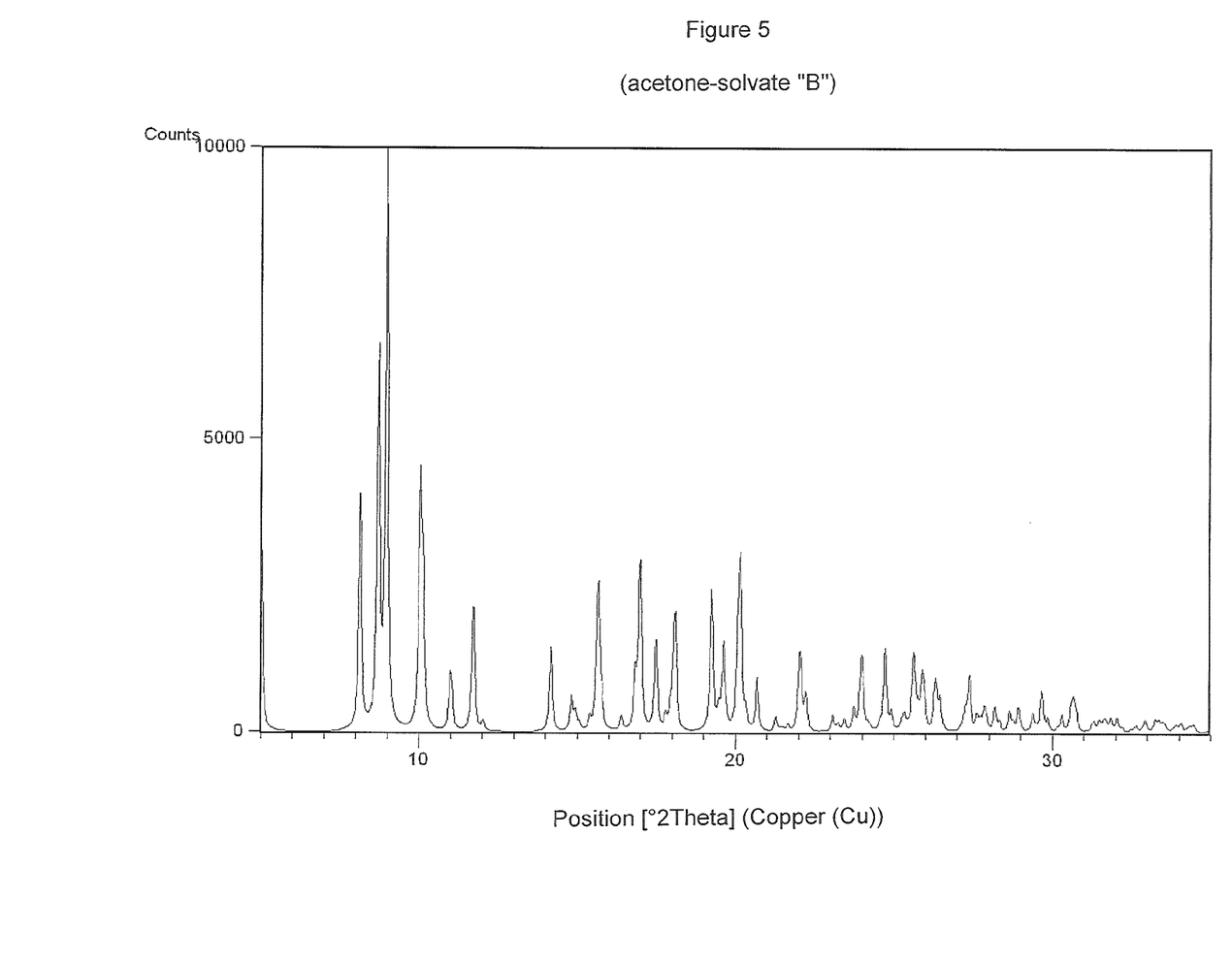
FIG. 5 shows an X-ray powder diffractogram of the crystalline acetone-solvate "B" of compound I. The X-ray powder diffractogram was recorded under the conditions stated in the following.

The crystallization product exhibited the X-ray powder diffractogram shown in FIG. 5.

Example 5

Preparation of the Acetone-Solvate "C" of Compound I

In a vial 500 mg of 6,6'-[[3,3',5,5'-tetrakis(1,1-dimethylethyl)-[1,1'-biphenyl]-2,2'-diyl]bis(oxy)]-bis-dibenzo[d,f][1,3,2]-dioxaphosphepine were solved in 20 ml of acetone. The vial with clear solution was sealed and subjected to heating/cooling cycles from 10° C. to 40° C. for 10 times. After 10 cycles crystal formation was observed in the solution. Then a suitable crystal was isolated under the microscope and subjected to X-ray structure elucidation.

Cell: triclinic P-1, Z=2, Z'=1; a=11.568(3) Å, b=12.738(3) Å, c=16.419(4) Å; α=95.632(10), β=90.723(9), γ=92.197(10); v=2405.6(10) Å$^3$, R-factor=3.6%.

Figure 6:
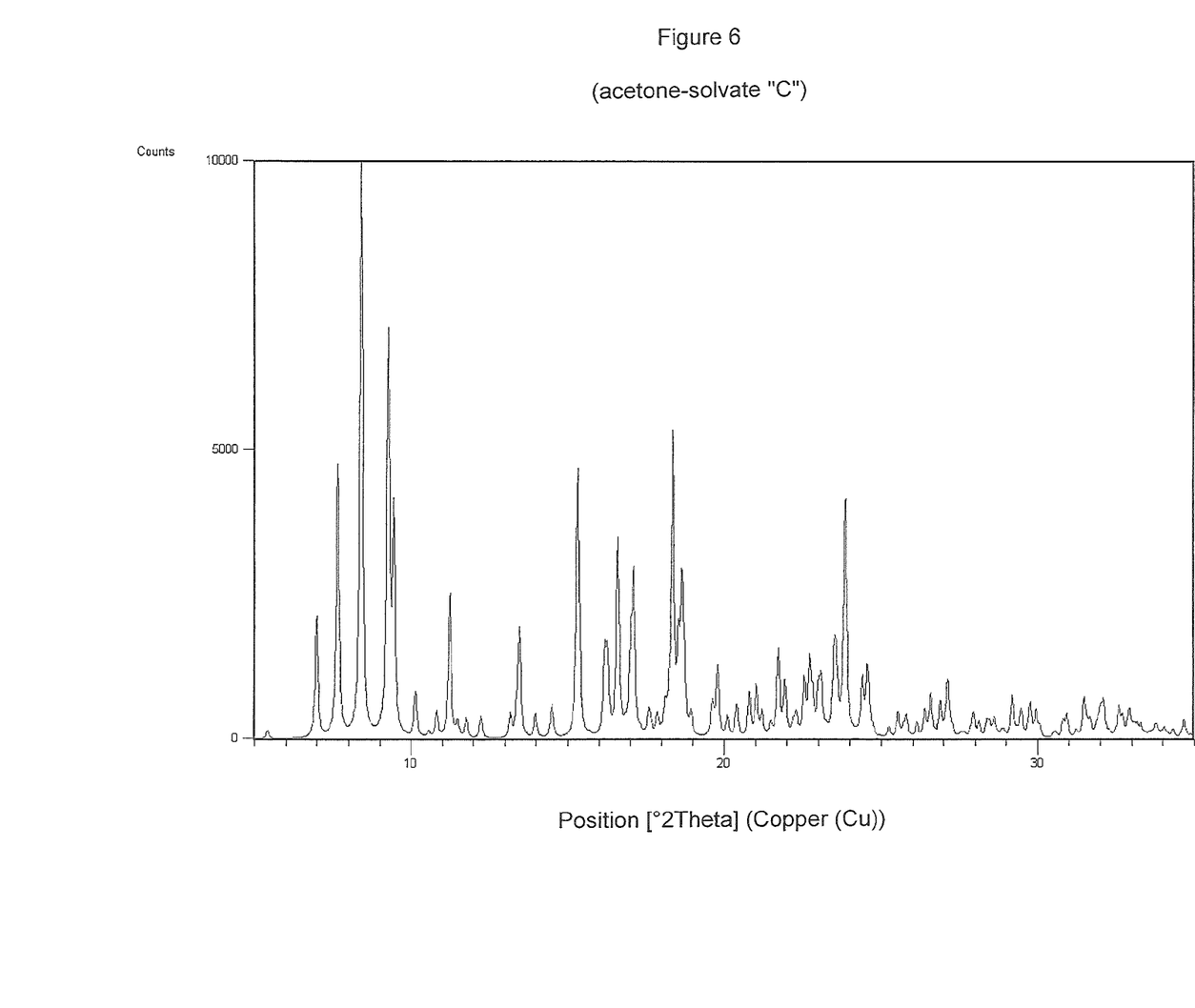
FIG. 6 shows an X-ray powder diffractogram of the crystalline acetone-solvate "C" of compound I. The X-ray powder diffractogram was recorded under the conditions stated in the following.

The crystallization product exhibited the X-ray powder diffractogram shown in FIG. 6.

Example 6

Preparation of the Toluene-Monosolvate of Compound I on a Technical Scale

A 2 L jacketed glass reactor was charged under an inert atmosphere with 6-chloro-dibenzo[d,f][1,3,2]-dioxaphosphepin (445.6 g of a solution 90% by weight in toluene, 1.60 mol), and this solution was heated to 85° C. Meanwhile, a 2 L Erlenmeyer flask with magnetic stirrer bar was charged with 1-methylimidazole (141.0 g, 1.60 mol) and toluene (791.5 g). 3,3',5,5'-Tetra-(1,1-dimethylethyl)-1,1'-biphenyl-2,2'-diol (320.5 g, 0.78 mol) was added to the stirred mixture resulting in an almost colourless solution. This solution was added via dropping funnel under an inert atmosphere within 80 minutes into the glass reactor. The brown-coloured reaction mixture that had formed was kept at 80° C. for another 50 minutes. Then, the mixture was heated to 90° C., and after stirring for another ten minutes, the stirrer was stopped. Two phases had formed, and were allowed to separate for 70 minutes. The lower layer (1-methyl imidazolium hydrochloride) was removed through the bottom valve to give 182.7 g of a viscous liquid which readily solidified (m.p. is ca. 80° C.). The upper phase was heated at reflux (115° C.) and stirred for three more hours. In the meantime, a 4 L jacketed glass reactor with stirrer was set up underneath the 2 L reactor in such a way that the bottom outlet of the 2 L reactor was connected via thermally insulated Teflon tubing through a neck of the 4 L reactor. The 4 L reactor was charged under an inert atmosphere with methanol (2000 ml), which was cooled to 20° C. The stirrer was then set to 355 rpm, and the toluene solution of the ligand from the 2 L reactor was run within 70 minutes through the Teflon tubing into the methanol in such a way that the stream coming off the Teflon tubing contacted neither the walls of the 4 L reactor nor the axis or the blades of the stirrer. The product precipitated instantly as a white solid, and after complete addition of the ligand solution the resulting suspension of the product was kept stirring at 20° C. for another hour. The product was filtered off, and the 4 L reactor rinsed with methanol (1000 ml). The methanol washings were transferred onto the filter cake, which was re-suspended and filtered again. After three more washings with methanol (1000 ml each portion), the filter cake was dried under suction and the product obtained was dried overnight at 70° C./10 mbar to give 605.3 g of a colourless, freely flowing powder. The product obtained directly after filtration was the toluene-monosolvate of 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepine.

Depending on the severity of the drying conditions the toluene-monosolvate can be converted into the non-solvated form of I. The toluene-monosolvate and mixtures of these two forms of I with varying composition depending on drying conditions are flowing freely and do not tend to baking on prolonged storage.

Chloride (ionic chromatography) 2 mg/kg,
nitrogen (ASTM D 5762-02) 4 mg/kg.

The invention claimed is:

1. A crystalline non-solvated form of 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepine (compound I) and toluene-solvates and acetone-solvates thereof.

2. A crystalline toluene-monosolvate of 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepine, which in an X-ray powder diffractogram at 25° C. with Cu—Kα radiation displays at least 5 of the following reflections, stated as 2θ values: 5.15±0.20°, 7.59±0.20°, 8.56±0.20°, 8.80±0.20°, 8.97±0.20°, 9.65±0.20°, 10.55±0.20°, 11.47±0.20°, 14.76±0.20° and 15.35±0.20.

3. A non-solvated crystalline form of 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepine, which in an X-ray powder diffractogram at 25° C. with Cu—Kα radiation displays at least 5 of the following reflections, stated as 2θ values: 5.39±0.20°, 7.04±0.20°, 8.44±0.20°, 8.65±0.20°, 9.08±0.20°, 9.66±0.20°, 10.66±0.20°, 12.60±0.20°, 16.25±0.20° and 17.36±0.20°.

4. The crystalline form as claimed in claim 3, wherein the crystalline form exhibits in the differential scanning calorimetry a peak attributed to the melting at 243° C.

5. A crystalline acetone-solvate "A" of 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepine, which in an X-ray powder diffractogram at 25° C. with Cu—Kα radiation displays at least 5 of the following reflections, stated as 2θ values: 6.67±0.20°, 7.11±0.20°, 7.87±0.20°, 8.31±0.20°, 8.96±0.20°, 9.17±0.20°, 10.68±0.20°, 15.78±0.20°, 16.10±0.20° and 18.63±0.20°.

6. A crystalline acetone-solvate "B" of 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepine, which in an X-ray powder diffractogram at 25° C. with Cu—Kα radiation displays at least 5 of the following reflections, stated as 2θ values: 8,13±0,2, 8,70±0,2°, 8,95±0,2°, 10,02±0,2°, 10,98±0,2°, 11,71±0,2°, 14,16±0,2°, 15,65±0,2°, 16,98±0,2° and 18,08±0,2°.

7. A crystalline acetone-solvate "C" of 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepine, which in an X-ray powder diffractogram at 25° C. with Cu—Kα radiation displays at least 5 of the following reflections, stated as 2θ values: 5.40±0.20°, 6.97±0.20°, 7.64±0.20°, 8.39±0.20°, 9.24±0.20°, 9.44±0.20°, 11.23±0.20°, 13.46±0.20°, 15.32±0.20° and 18.35±0.20°.

8. A composition comprising at least 75% by weight of at least one crystalline form of the compound I as defined in claim 1.

9. A composition comprising at least 95% by weight, based on the total weight of the composition, of at least one crystalline form of the compound I as defined in claim 1.

10. A composition comprising at least two crystalline forms, selected from
a crystalline toluene-monosolvate of 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepine,
which in an X-ray powder diffractogram at 25° C. with Cu—Kα radiation displays at least 5 of the following reflections, stated as 2θ values: 5.15±0.20°, 7.59±0.20°, 8.56±0.20°, 8.80±0.20°, 8.97±0.20°, 9.65±0.20°, 10.55±0.20°, 11.47±0.20°, 14.76±0.20° and 15.35±0.20,
a non-solvated crystalline form of 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepine, which in an X-ray powder diffractogram at 25° C. with Cu—Kα radiation displays at least 5 of the following reflections, stated as 2θ values: 5.39±0.20°, 7.04±0.20°, 8.44±0.20°, 8.65±0.20°, 9.08±0.20°, 9.66±0.20°, 10.66±0.20°, 12.60±0.20°, 16.25±0.20° and 17.36±0.20°,
a crystalline acetone-solvate "A" of 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepine, which in an X-ray powder diffractogram at 25° C. with Cu—Kα radiation displays at least 5 of the following reflections, stated as 2θ values: 6.67±0.20°, 7.11±0.20°, 7.87±0.20°, 8.31±0.20°, 8.96±0.20°, 9.17±0.20°, 10.68±0.20°, 15.78±0.20°, 16.10±0.20° and 18.63±0.20°,
crystalline acetone-solvate "B" of 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepine, which in an X-ray powder diffractogram at 25° C. with Cu—Kα radiation displays at least 5 of the following reflections, stated as 2θ values: 8,13±0,2°, 8,70±0,2°, 8,95±0,2°, 10,02±0,2°, 10,98±0,2°, 11,71±0,2°, 14,16±0,2°, 15,65±0,2°, 16,98±0,2° and 18,08±0,2°, or the acetone-solvate "C" as defined in claim 7.

11. A process for the preparation of the crystalline toluene-monosolvate of compound I, as defined in claim 2, comprising:
- i) preparing a solution of compound I in toluene which is supersaturated at a temperature of 30° C., and
- ii) allowing compound I to crystallize at a temperature of not more than 30° C.

12. The process according to claim 11, wherein in step i) a saturated solution of compound I at a temperature of at least 80° C. is prepared.

13. The process according to claim 11, wherein in step i) a saturated solution of compound I at reflux temperature, is prepared.

14. The process according to claim 11, wherein the crystallization in step ii) is performed by cooling a solution of compound I in toluene to a temperature of not more than 30° C., wherein the solution has a concentration of compound I that it is supersaturated at a temperature of not more than 30° C.

15. The process according to claim 11, wherein the crystallization in step ii) is performed by adding the solution of compound I in toluene having a temperature of about at least 65° C. to a vessel containing methanol having a temperature of not more than 30° C., and wherein during the addition and the crystallization the temperature of the solvent-mixture in the vessel is kept at a value of not more than 30° C.

16. A process for the preparation of the non-solvated crystalline form of compound as claimed in claim 3, wherein 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepine is allowed to crystallized at a temperature of above 65° C. or wherein 6,6'-[[3,3',5,5'-tetrakis(1,1-dimethylethyl)-[1,1'-biphenyl]-2,2'-diyl]bis(oxy)]bis-dibenzo[d,f][1,3,2]-dioxaphosphepine which comprises suspending in a solvent and the suspended material is agitated in the suspension at a temperature of at least 65° C.

17. The process according to claim 16, wherein the solvent is selected from toluene, di-n-butylether and mixtures thereof.

18. The process according to claim 16, wherein the suspension time is at least 10 minutes.

19. The process according to claim 16, wherein the suspension time is at least 1 hour.

20. The process according to claim 16, wherein the suspension is separated from the mother liquor at a temperature of at least 65° C.

21. A process for the preparation of the crystalline acetone-solvate "A" of compound I as claimed in claim 5, comprising:
- I) preparing a suspension of compound I in acetone,
- II) heating the suspension to bring compound I into solution, and
- III) cooling the solution obtained in step II) and performing a crystallization.

22. A process for the preparation of the crystalline acetone-solvate "B" of compound I as claimed in claim 6, comprising:
- I) providing a solution of compound I in acetone, and
- II) allowing a part of the solvent of the solution provided in step I to evaporate and thus allowing compound I to crystallize.

23. A method to obtain the crystalline acetone-solvate "C" of compound I as claimed in claim 7, comprising:
- I) preparing at a temperature of from about 15 to 25° C. a saturated solution of compound I in acetone,
- II) warming the obtained solution to a temperature that is about 15 to 25° C. higher than the temperature in step I), and
- III) allowing the solution obtained in step II) to cool to a temperature that is about 5 to 15° C. below the temperature of step I), wherein steps I) to III) are repeated for at least 10 times.

24. A process for the production of a transition metal catalyst for hydroformylation, hydrocyanation or hydrogenation which comprises utilizing crystalline form of compound I, as claimed in claim 1.

25. A method for producing a transition metal catalyst which comprises providing and bringing into contact a crystalline form of compound I as claimed in claim 1 with a compound or a complex of a transition metal in an inert solvent.

26. The method according to claim 25, wherein the transition metal is selected from among metals of the groups 8, 9 or 10 of the periodic table of the elements.

27. The method according to claim 25, wherein the transition metal is rhodium, cobalt or nickel.

28. A transition metal catalyst obtained by the method of claim 25.

* * * * *